(12) United States Patent
Carlsson et al.

(10) Patent No.: US 11,241,546 B2
(45) Date of Patent: Feb. 8, 2022

(54) HOLDER FOR A RECORDING UNIT

(71) Applicant: SHL MEDICAL AG, Zug (CH)

(72) Inventors: Daniel Carlsson, Enskede (SE); Rasmus Renstad, Stockholm (SE); Christina Mansjö, Stockholm (SE)

(73) Assignee: SHL MEDICAL AG, Zug (CH)

( * ) Notice: Subject to any disclaimer, the term of this patent is extended or adjusted under 35 U.S.C. 154(b) by 432 days.

(21) Appl. No.: 16/330,369

(22) PCT Filed: Aug. 18, 2017

(86) PCT No.: PCT/EP2017/070948
§ 371 (c)(1),
(2) Date: Mar. 4, 2019

(87) PCT Pub. No.: WO2018/046282
PCT Pub. Date: Mar. 15, 2018

(65) Prior Publication Data
US 2021/0275758 A1    Sep. 9, 2021

(30) Foreign Application Priority Data

Sep. 7, 2016  (EP) .................................... 16187704

(51) Int. Cl.
| | |
|---|---|
| *A61M 5/50* | (2006.01) |
| *G16H 10/60* | (2018.01) |
| *G16H 10/65* | (2018.01) |
| *G06Q 10/10* | (2012.01) |

(52) U.S. Cl.
CPC .......... *A61M 5/5086* (2013.01); *G06Q 10/10* (2013.01); *G16H 10/60* (2018.01); *G16H 10/65* (2018.01); *A61M 2205/0216* (2013.01); *A61M 2205/3561* (2013.01); *A61M 2205/3569* (2013.01); *A61M 2205/502* (2013.01); *A61M 2205/52* (2013.01); *A61M 2205/583* (2013.01); *A61M 2209/086* (2013.01)

(58) Field of Classification Search
None
See application file for complete search history.

(56) References Cited

U.S. PATENT DOCUMENTS

| | | | |
|---|---|---|---|
| 2002/0096543 A1 | 7/2002 | Juselius | |
| 2011/0288481 A1* | 11/2011 | Mudd | ..................... A61M 5/20 604/131 |
| 2015/0097701 A1* | 4/2015 | Al-Ali | ..................... G06F 21/84 340/870.07 |

FOREIGN PATENT DOCUMENTS

| | | |
|---|---|---|
| DE | 202014106129 U1 | 3/2015 |
| WO | 2008/045203 A1 | 4/2008 |
| WO | 2014/118111 A1 | 8/2014 |

\* cited by examiner

*Primary Examiner* — Kristy A Haupt
(74) *Attorney, Agent, or Firm* — McDonnell Boehnen Hulbert & Berghoff LLP

(57) ABSTRACT

The present disclosure relates to a holder for a recording unit, which recording unit is arranged with an interface configured to cooperate with an interface of a medicament delivery device for obtaining information regarding the use of the medicament delivery device, the holder has an interface configured to cooperate with the interface of the recording unit, and the holder further has attachment elements for attaching the holder to a suitable surface.

19 Claims, 9 Drawing Sheets

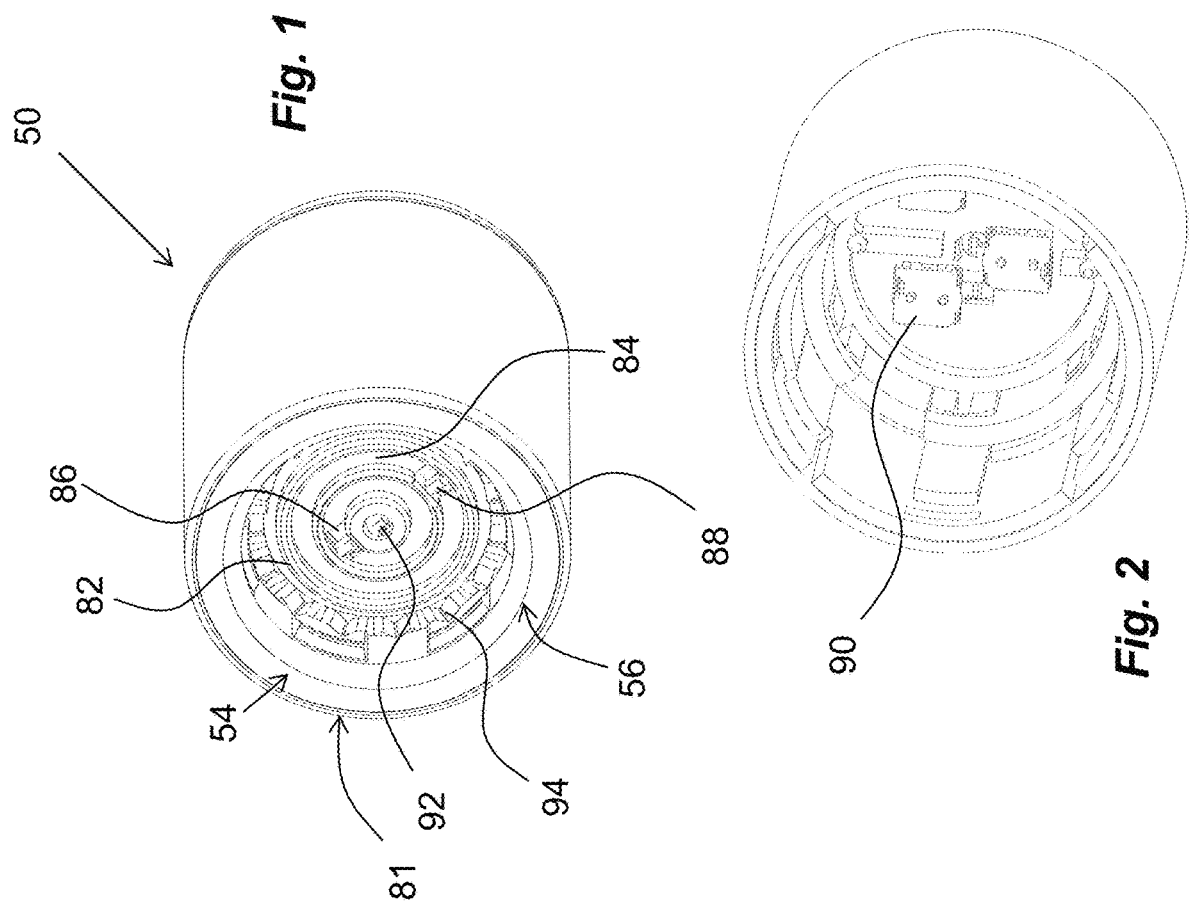
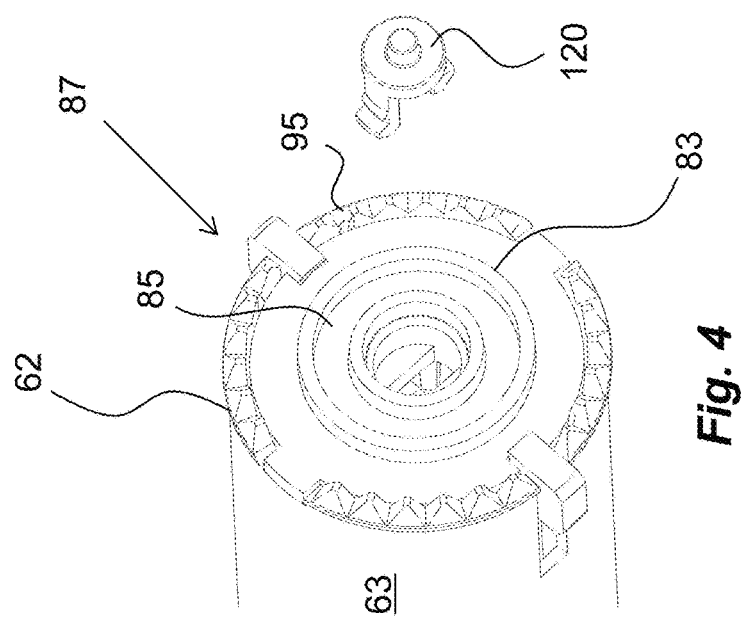

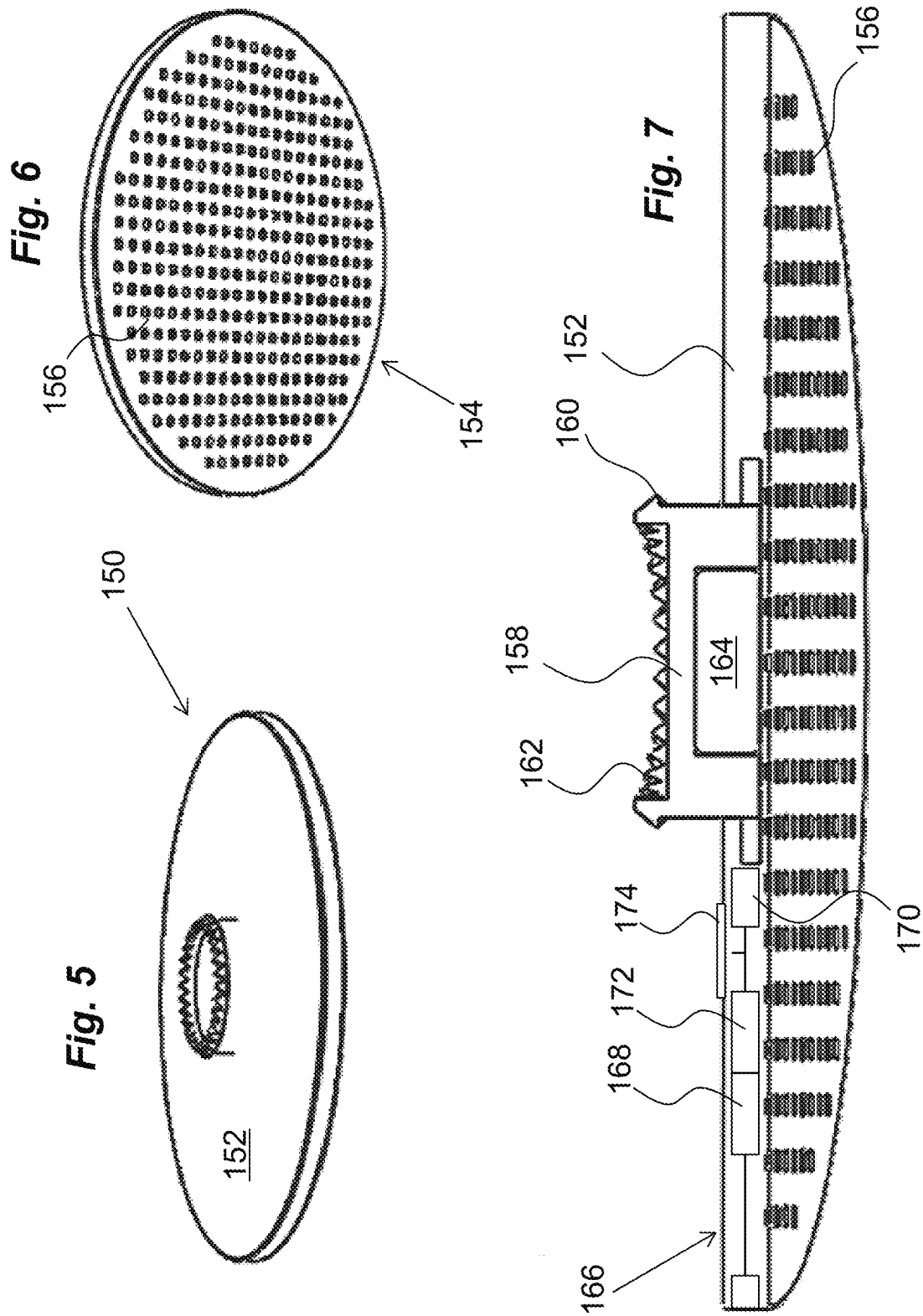

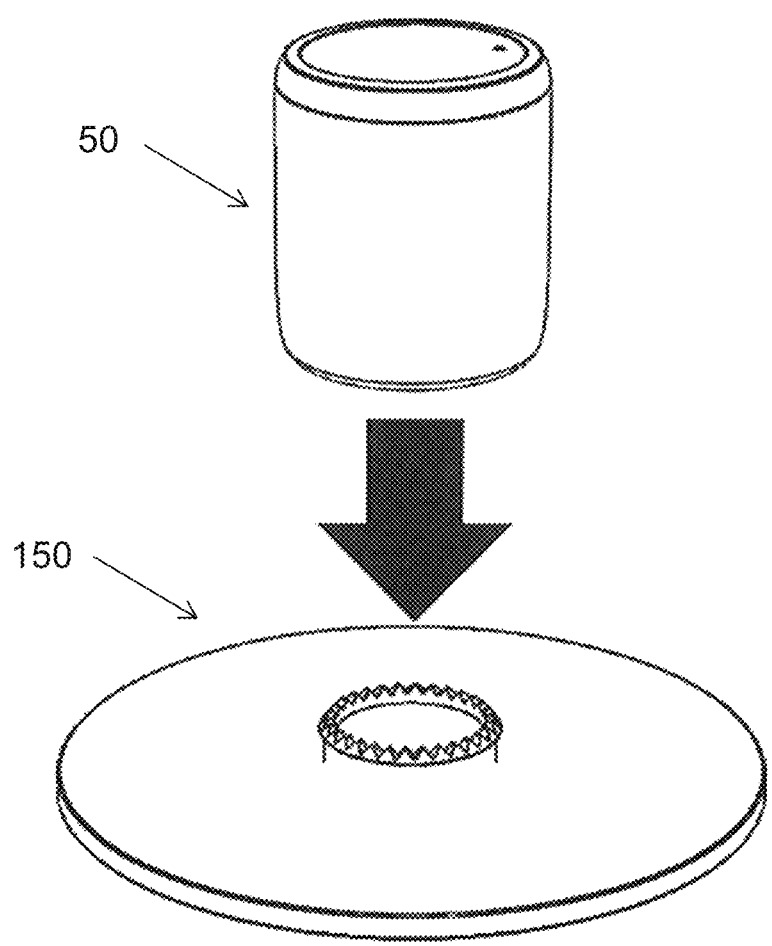

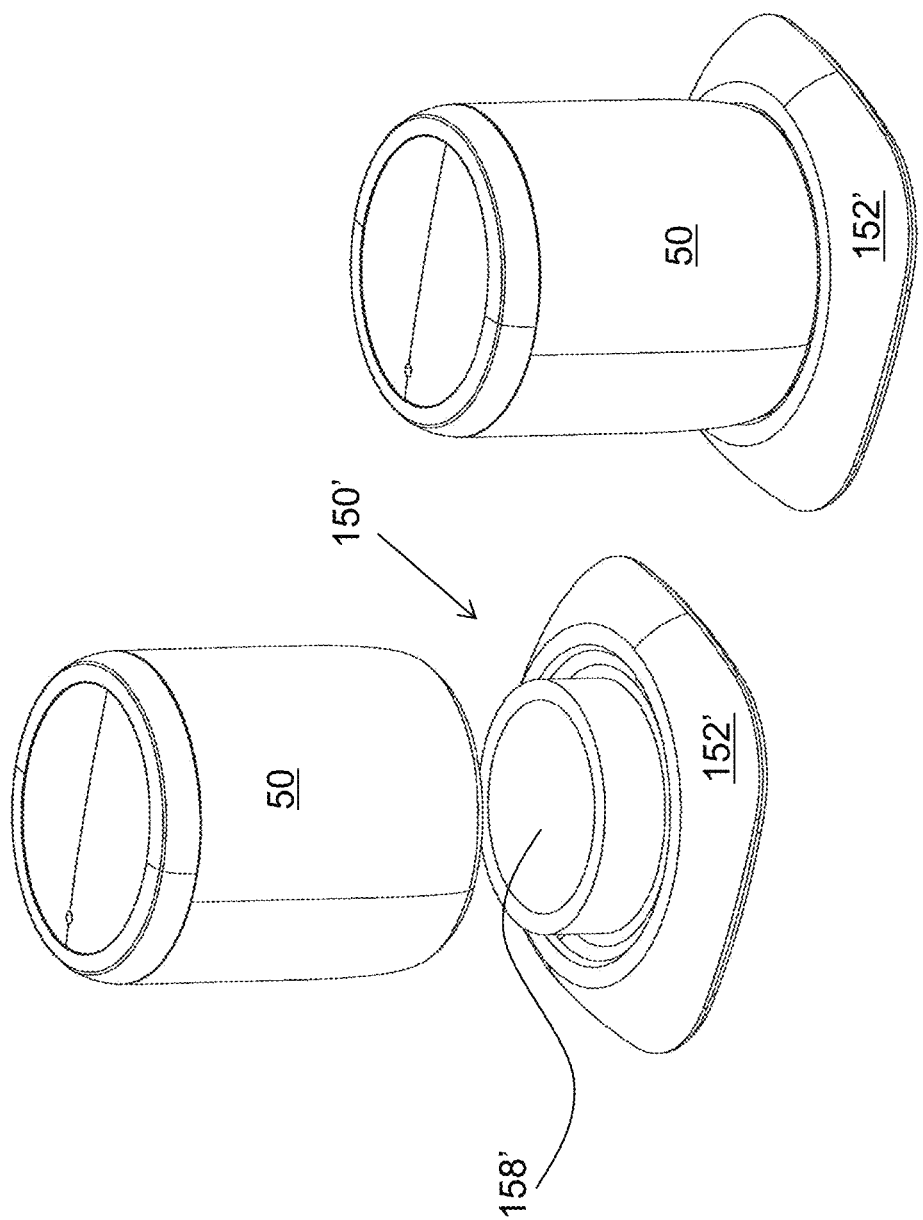

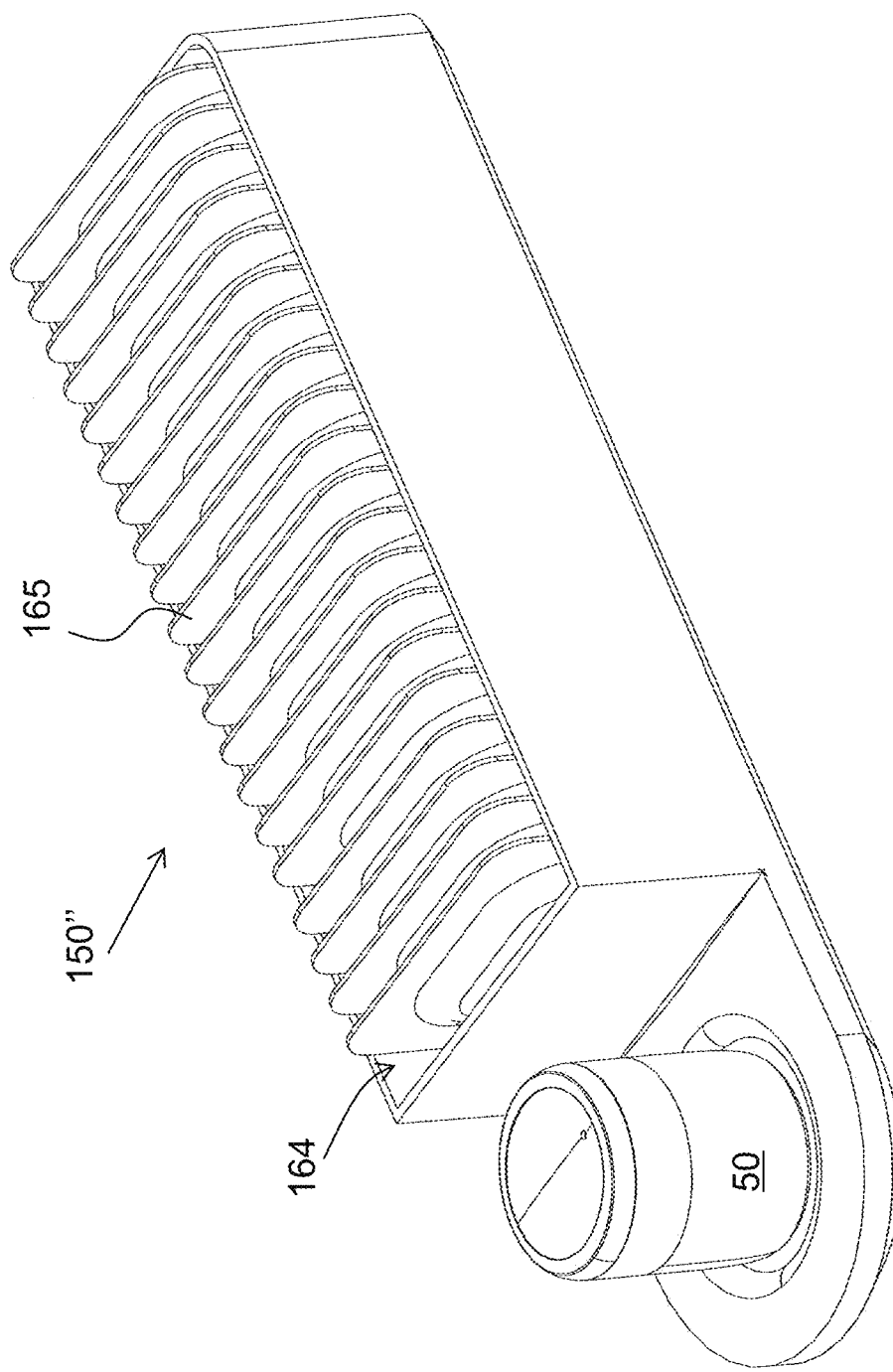

HOLDER FOR A RECORDING UNIT

CROSS REFERENCE TO RELATED APPLICATIONS

The present application is a U.S. National Phase Application pursuant to 35 U.S.C. § 371 of International Application No. PCT/EP2017/070948 filed Aug. 18, 2017, which claims priority to European Patent Application No. 16187704.8 filed Sep. 7, 2016. The entire disclosure contents of these applications are herewith incorporated by reference into the present application.

TECHNICAL AREA

The present disclosure relates to a holder that can releasibly hold a recording unit, wherein the recording unit is used in conjunction with a medicament delivery device for monitoring and obtaining data regarding the use of the medicament delivery device.

BACKGROUND

There is a constantly growing demand for monitoring the behaviour of a patient that is self-medicating according to treatment schemes in order to ascertain that the patient is following the scheme, i.e. is adhering. If not, the patient may be alerted by the physician responsible and appropriate steps may be taken.

Many of the medicament delivery devices on the market for self-administration are so called disposables, i.e. they are discarded after use. For this type of medicament delivery device it is a challenge to provide it with recording units because they are used only once. The recording units often comprise electronic circuits with sensor and communication elements and are often driven by small power sources like button cells. It would be too costly to include a recording unit that is only used one time and it is also environmentally not acceptable to throw away electronic equipment and power cells without proper recycling. The latter is problematic since the medicament delivery device is regarded as bio-hazardous waste that has to be handled with special measures, like discarding them in sharps containers.

In view of this, recording units have been developed that are re-usable. This means that they can be connected to a disposable medicament delivery device during delivery of the medicament and after user, the recording unit is removed and the medicament delivery device is discarded. The recording unit is then stored until the next scheduled medicament delivery occurrence. However, this may cause problems if for example a medicament is to be administered with long periods between the occurrences, like once or twice a month, or even once a week. At the time of medicament delivery, the patient might have forgotten where he or she has placed the recording unit, which then might lead to that the patient uses the medicament delivery device without the recording unit, which in turn means that the medicament delivery is not monitored and recorded, giving a wrong indication that the patient is not adhering to the prescribed scheme.

SUMMARY

The aim of the present disclosure is to remedy the drawbacks of the state of the art designs. The solution is to provide a holder provided with the features of the independent patent claim. Preferable embodiments of the disclosure form the subject of the dependent patent claims.

According to a main aspect of the disclosure, it comprises a holder for a recording unit, which recording unit is arranged with an interface configured to cooperate with an interface of a medicament delivery device for obtaining information regarding the use of the medicament delivery device, the holder comprising an interface configured to cooperate with the interface of the recording unit, and the holder further comprising attachment elements for attaching the holder to a suitable surface.

One advantage with this solution is that the holder facilitates the storage of a recording unit when it is not used together with a medicament delivery device. It is particularly advantageous for recording units that are used with disposable medicament delivery devices since these types of medicament delivery devices are to be discarded as soon as possible after use in order to minimize the risk of accidental needle sticks. Then the recording unit has to be removed from the medicament delivery device after use. The holder according to the disclosure then provides a natural and obvious place for the recording unit to be placed after use and retrieved for subsequent use.

Since the holder preferably is arranged with appropriate attachment elements, it may be placed securely on specific locations and surfaces, thereby reducing the risk of damaging the recording unit should the holder and the recording unit be exposed to sudden forces.

According to one aspect of the disclosure, it may further comprise a stand provided with an interface, onto which the recording unit may be removably attached. With such a solution, a positive, form-functioning connection interface is obtained, which preferably may correspond to the connection interface of a medicament delivery device to which the recording unit may be attached. In this regard, the interfaces may comprise 3-D structures configured to positively engage with each other.

The holder may further comprise a base, which base is arranged with said attachment elements. According to one feasible aspect, the base may be arranged in a material flexible so as to adapt to the shape of the attaching surface. This will then facilitate the attachment on surfaces that are curved and not only to planar surfaces.

Regarding the attachment elements, a number of possible elements and functions may be utilized. For instance the attachment elements may comprise a number of suction cups. As an alternative the attachment elements may comprise micro-porous material. These types of attachment elements provide a releasable attachment of the holder to a suitable surface, providing the possibility of placing the holder at different locations depending on the user's preference.

As another alternative the attachment elements may comprise adhesive tape. Further, the attachment elements comprise hooks and loops. With these types of attachment elements, a more permanent attachment position is obtained, especially when adhesive tape is used. If hooks and loops are used, then one part may be attached to a number of positions where the user wants the holder to be placed, enabling a choice of positions.

As a further possibility the attachment elements may comprise a number of magnets. With this solution, the holder may be connected to magnetic surfaces such as steel sheets that form the outer surface of for example household appliances and in particular refrigerators. This is particularly advantageous since on the one hand the kitchen is a central place of a residence where people spend a lot of time, facilitating remembering to take a dose of medicament when the user sees the recording unit. On the other hand, many medicament delivery devices are stored in refrigerators in order to preserve the quality of the medicament. It is thus a natural place to store the recording unit on the refrigerator door close to the medicament delivery devices.

According to a further aspect of the disclosure, the holder may comprise an electronic circuit arranged operably connected to said recording unit when attached to the holder. The electronic circuit of the holder may then be used together with the electronic circuit of the recording unit for performing a number of additional functions. In that regard, the electronic circuit of the holder may be arranged with user communication elements. One way of monitoring and obtaining data of how a patient or user is perceiving the treatment is to provide the user communication elements of the holder with buttons where each button is indicative of the perceived health of the patient. After each use of a medicament delivery device when returning the recording unit to the holder, the user then presses one of the buttons on the holder, choosing a specific button depending on how the patient feels.

According to a further aspect, the user communication elements may comprise at least one display. The display may be used for communicating different status information such as time to next dose, which drug to be taken if the user has more than one medicament that is administered via medicament delivery devices, etc.

These and other aspects of, and advantages with, the present disclosure will become apparent from the following detailed description of the disclosure and from the accompanying drawings.

BRIEF DESCRIPTION OF THE FIGURES

In the following detailed description of the disclosure, reference will be made to the accompanying drawings, of which FIGS. 1-3 is an example of a recording unit arranged to cooperated with the present disclosure, FIG. 2 is another example of a recording unit arranged to cooperated with the present disclosure, FIG. 3 is yet another example of a recording unit arranged to cooperated with the present disclosure, FIG. 4 shows a distal end of a medicament delivery device arranged with an interface intended to cooperate with a corresponding attachment interface of the recording unit of FIGS. 1-3, FIG. 5 is a perspective view from above of a holder according to the disclosure, FIG. 6 is a perspective view from below of the holder of FIG. 5, FIG. 7 is a cross-sectional view of the holder of FIG. 5, FIG. 8 shows the connection of the recording unit to a holder, FIG. 10 shows a variant of the holder of FIG. 5 arranged with user communication elements, FIGS. 12 shows the holder of the present disclosure arranged a storage compartment.

DETAILED DESCRIPTION

Figure 3:
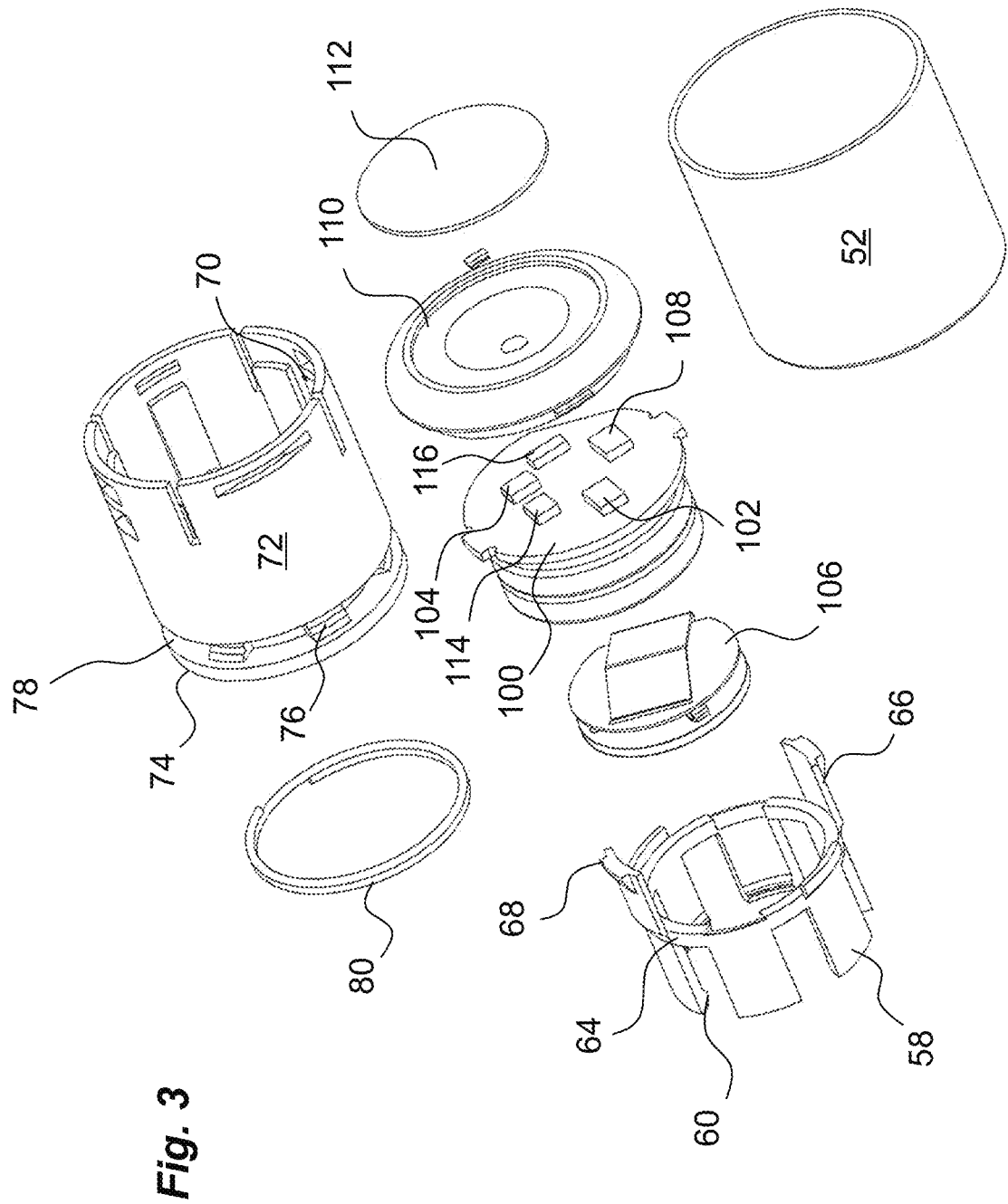

FIGS. 1-3 show an example of a recording unit 50 arranged to be operably connected to a medicament delivery device. The recording unit 50 comprises a housing 52 that might have a corresponding shape and appearance as a medicament delivery device. The housing 52 has a proximally directed attachment mechanism 54 that is designed to interact with for instance a distal end of the medicament delivery device. In the embodiment shown, the attachment mechanism 54 comprises a central passage 56 which has a shape and dimension so as to fit onto the distal end of the medicament delivery device.

In order for the connection to be releasable, the attachment mechanism 54 of the recording unit 50 comprises locking elements in the form of a number of attachment tongues 58, FIG. 3, that are flexible in the generally radial direction. The free ends of the attachment tongues 58 are arranged with inwardly directed ledges 60 that may be designed to cooperate with corresponding locking elements in the form of an annular ledge 62 at the distal end of the housing of a medicament delivery device 63. The attachment tongues 58 are attached to a ring-shaped element 64, which ring-shaped element 64 is arranged with two oppositely positioned, distally directed, tongues 66. The free ends of the tongues 66 are arranged with outwardly directed ledges 68, which ledges are arranged to fit into recesses 70 in a tubular holding member 72.

The holding member 72 is arranged with a plate-shaped contact element 74 at its proximal end, where the holding member 72 and the contact element 74 are interconnected by a number of bridges 76. The bridges 76 are placed somewhat radially inwards in relation to the holding member 72 such that an annular recess 78 is formed. Further, in the spaces between the bridges 76 the free ends of the attachment tongues 58 are placed. The attachment tongues 58 and the bridges 76 are designed and positioned such that the outer surfaces of the tongues 58 are placed somewhat radially outside the bridges 76. Further a wire spring 80 is arranged in the annular recess 78, whereby it is in contact with the outer surface of the attachment tongues 58, providing a resilient force in the outwards radial direction.

The recording unit 50 may further be arranged with a mechanical interface 81, FIG. 1. The mechanical interface may comprise a number of rings 82 and grooves 84 on the proximally directed surface of the contact element 74 having a design that fits together with rings 83 and grooves 85, FIG. 5, of the distal end of the medicament delivery device 63 that the recording unit 50 is to be connected to, forming a contact interface. Further, the contact element 74 is preferably arranged with a number of passages 86, in which passages 86 switches 88 are placed. The switches 88 are operably connected to electrical switching elements 90, FIG. 2, that will enable activation of the recording unit 50 as will be described. Preferably the switches 88 are arranged and designed to interact with the contact surface 87 such that the switches 88 are activated when the recording unit 50 is attached. Preferably the positions of the switches 88 of the electrical switching elements are arranged in a certain pattern that can be specific for a certain recording unit and wherein a certain contact surface 87 has the same design so that all switches 88 are activated when the recording unit is attached.

For example the contact surfaces are the rings and grooves wherein the switches 88 are positioned at different distances in a radial direction as seen in FIG. 1. The advantage with having rings is that the angular position between the recording unit and the contact surface is not important when the two are interconnected. Further, as seen in FIG. 1, since the switches 88 are placed in the grooves 84, manipulation of the switches 88 by fingers is difficult, providing increased security against improper use of the recording unit 50.

Further, in order to automatically activate the recording unit 50 at the point of contact with the medicament delivery device, the recording unit 50 may be provided with an activation switch 92. In the embodiment shown in FIG. 2, this activation switch 92 may be placed in a central position of the interface of the recording unit 50.

The interface between the contact surface and the recording unit 50 could further comprise mechanical patterns that are to interact with each other. For instance the proximal surface of the contact element 74 could comprise a number of teeth 94 for example around a circumference. These teeth 94 are arranged to cooperate with corresponding teeth 95 on the medicament delivery device, wherein the number of teeth, the design of the teeth and the positions of the teeth are chosen such that a keying function is obtained. Thus, only recording units and medicament delivery devices that have the same pattern can be inter-connected. This provides the possibility of customizing the recording unit 50 such that only certain connections are possible.

The recording unit shown in the drawings may further comprise an electronic circuit 100 comprising a processor 102, FIG. 3, capable of processing data program code for performing different tasks. The data program code is preferably stored in appropriate memory elements 104, in which also retrieved data may be stored, as will be described. The electronic circuit 100 is further arranged with some power supply 106 such as button cells, photovoltaic panels, etc. Further, the above mentioned switching elements 90, 92 are electronically connected to the electronic circuit 100. In this respect it might be that all switches need to be operated at the same time in order for the recording unit to be activated. The electronics circuit may further be arranged with user communication elements 108 that is arranged and programmed to communicate with a user. The user communication elements 108 may comprise display elements that can communicate visually, e.g. by text stored in the electronics module that is displayed on a suitable display 110 on the recording unit. The display may be protected by a suitable transparent cover or glass 112. In addition to, or instead, the user communication circuit may comprise audio elements 114 that can communicate audibly, e.g. by a recorded message stored in the electronics module that is played in an appropriate loudspeaker of the electronics module or of the device as such.

A further development of the activation function is to provide the recording unit 50 with at least one communication circuit 116 comprised in the user communication elements. The communication technologies that the communication circuit 116 may utilize may comprise near range communication technology such as RFID, NFC or the like, as well as Bluetooth, Ant, ZigBee, just to mention a few. This type of wireless communication technology may also be used to activate the recording unit. The communication circuit may be used for monitoring the usage of the medicament delivery device such that information is transmitted from the medicament delivery device to the recording unit. Other types of communication technologies that are feasible are cellular radio communication networks, e.g. GSM, 3G, 4G, etc. and/or wireless local area networks, which networks can provide access to the internet and thus to a large number of external data storage sources, data handling centres, etc.

According to the disclosure, a holder 150 for a recording unit is provided, FIG. 5. The holder 150 may be arranged with a sheet-like base 152. Preferably the base 152 is arranged in a material that provides a certain flexibility in directions transversal to the plane of the base 152 such that the base 152 can adjust to somewhat curved surfaces and not only planar surfaces. Possible materials comprise rubber, plastic and the like materials that are elastically deformable. The underside 154 of the base 152 is preferably arranged with attachment elements 156 that are designed to interact with a surface to which the holder is to be placed on. For example the attachment elements may be formed as hooks and loops that can interact with corresponding hooks and loops of the surface. Other feasible attachment elements comprise a number of suctions cups capable of creating a negative fluid pressure when pressed onto the surface. Further variants may comprise microporous material, materials with adhesive properties such as e.g. double-sided adhesive tape. Other types of attachment elements may comprise magnets embedded in the base or stand or attached to the underside of the base, whereby the holder may be attached to magnetic metal surfaces.

Figure 9:
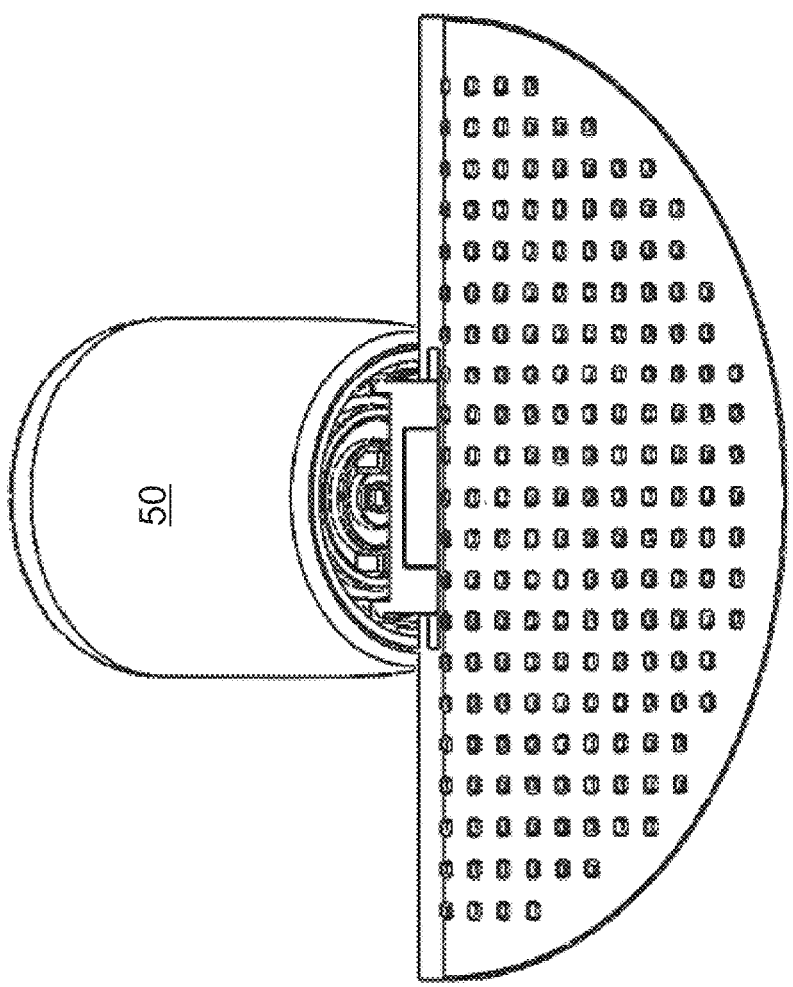
FIG. 9 shows a partly cross-sectional view of the recording unit connected to the holder.

The upper side of the base 152 is arranged with an attachment interface 158 designed as an upwardly directed stand. The stand 158 is designed so as to interconnect with the recording unit. In that regard the stand has an annular ledge 160 that is intended to engage the ledges 60 of the flexible tongues 58 of the recording unit 50, such that the recording unit is releasibly connected to the holder. Further an upwardly directed surface of the stand 158 is arranged with annular teeth 162 that are designed to engage with the teeth 94 of the recording unit 50. This provides a firm positive contact between the holder 150 and the recording unit 50. Also, due to the inter-connecting interfaces between the recording unit and the holder, the interface 81 of the recording unit with its switches is protected from dust and particles during storing as seen in FIG. 9.

FIG. 10 shows a variant on the holder 150' according to the disclosure. Here the stand 158' of the base 152' is not provided with any structure that has to mate with a corresponding structure of the recording unit 50. This provides the possibility of turning the recording unit in relation to the holder, the function of which will be described below.

The holder 150 may be placed on any suitable surface and suitable location so that it is easily retrievable by a user. For example, the holder 150 may be placed in the vicinity where the medicament delivery devices are stored. For example the medicament delivery devices may be stored in a medicament cupboard, wherein the holder may be placed on a suitable surface on the medicament cupboard. As an alternative, if the medicament delivery devices are stored in the refrigerator, as is the case for many medicament types, then the holder can be attached to the refrigerator door, see FIG. 10a. In this regard, the magnets are very convenient attachment elements since the refrigerators are often made of magnetic metals. The holder may also be placed where a user often is doing tasks such as in a bathroom, FIG. 10b, or on a bedside table, FIG. 10c. The suction functions of the attachment elements are then convenient for attaching the holder to for example a mirror or the upper surface of the bedside table. The holder 150" may be arranged with additional storage features such as for example storage compartments 164 for different products to be used together with administration of medicament, such as packages of sterile wipes 165 that are used to clean an injection site before administration as seen in FIG. 12.

In addition to the holding function, the holder 150 may further be arranged with an electronic circuit 166, FIG. 7, for instance a printed circuit board. The electronic circuit 166 is arranged with a micro-processor 168 arranged to handle and run program code for performing different functions as will be described. The micro-processor 168 is operably connected to a power source 170 of the electronic circuit. The power source 170 may be a battery such as a button cell, but can also or in addition, be a photovoltaic panel. The electronic circuit 14 is further arranged with storage elements or memory 172 that are adapted to store program code for the micro-processor 168. The holder 150 may also comprise user communication elements 174 that are capable of providing information. The user communication elements 174 may comprise input/output elements such as displays with or without touch function, speakers, lamps, switches or buttons, just to mention a few elements that can perform signalling functions. In the embodiment shown, the user communication elements comprise a number of buttons 176, FIG. 12, having symbols in the form of faces, from sad to glad faces. This may be used for collecting information how the patient is feeling during the treatments scheme, i.e. the perceived health of the patient. The processor may also be arranged with a clock or timer function so as to be able to keep track of time and date. Thereby, information can be obtained regarding when a user provides input to the stand, which may be utilized as info regarding adherence. The user communication elements may as mentioned comprise a display 178 that provides the user with information regarding e.g. adherence, time to next dose delivery etc.

Figure 11A:
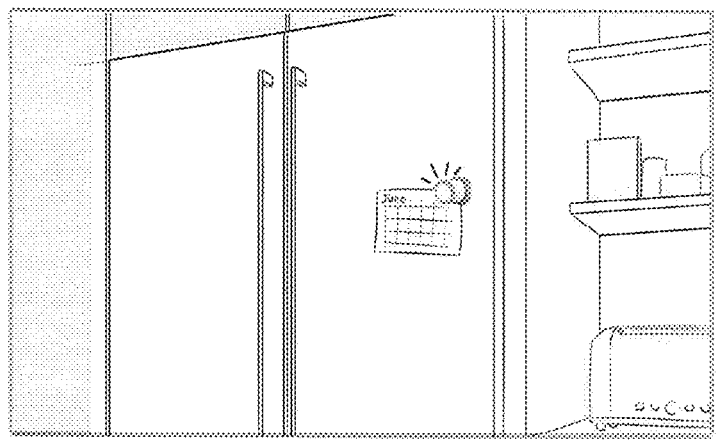
FIGS. 11A, 11B and 11C show the recording unit notifying a user with lights and/or sound.
Figure 11B:
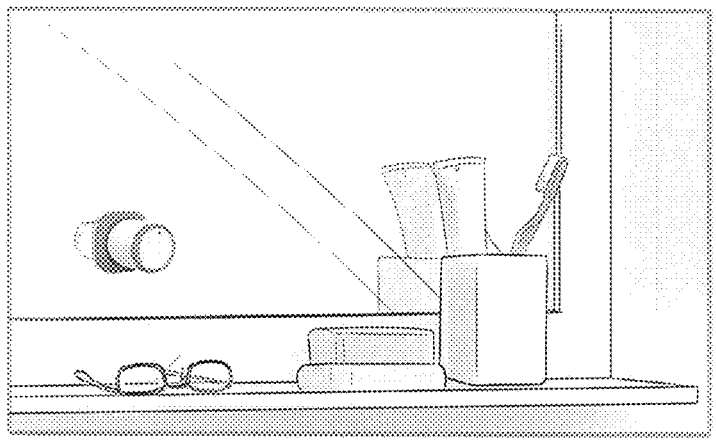
Figure 11C:
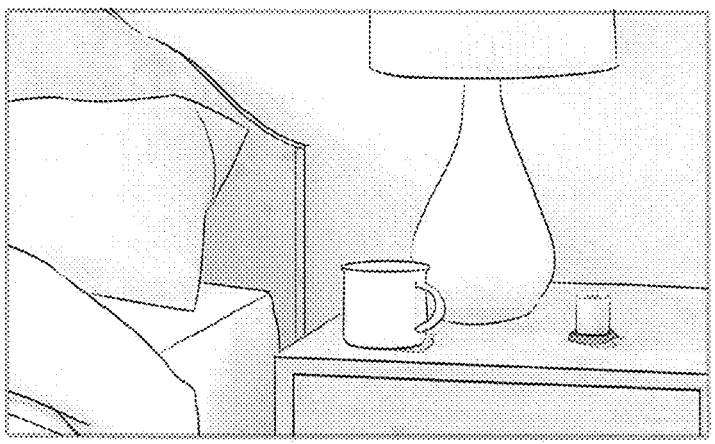
Figure 13:
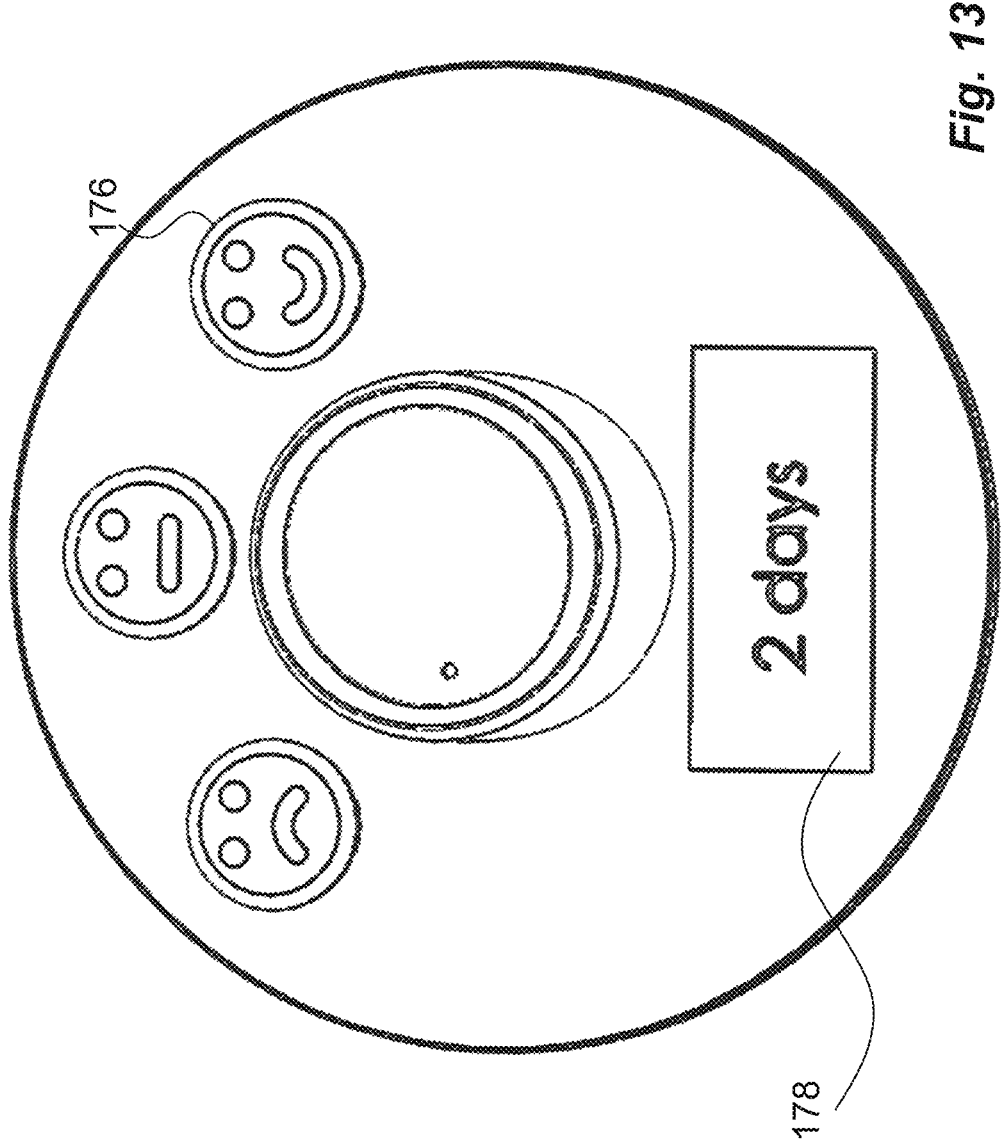
FIG. 13 shows the holder used with communication elements to collect information from a user.

The electronic circuit 166 may be used in connection with the recording unit 50 when the latter is connected to the holder. For instance, the activation of the electronics circuit 166 when a patient presses a button 176 on the holder, may in turn activate the recording unit and the activated recording unit may then be used to transmit information from the recording unit to for example a smart device without the patient needing to pick up the smart device and start a health application for instance. The smart device may also transmit data to external data bases for further processing. Also, the holder and the recording unit may work together for informing a user. For instance, the electronic circuit of the holder may for instance keep track when a dose of medicament is to be administered, and may activate the recording unit so that it informs the user. This may be done by lights on the recording unit as seen in FIG. 11a or by sound from the recording unit.

Further, the recording unit and the holder may work together for obtaining information and for inputting information in that the recording unit may be rotated when connected to the stand. The rotation may activate the electronic circuit of the holder such that different menus are displayed when the holder is turned. Pressing of the recording unit may then be used to input information from a user. The holder may further be arranged with a power source whereby the recording unit may be charged when connected to the holder. The power source may be a battery pack in the holder, a photovoltaic panel on the holder or a conventional electrical cord connectable to a mains socket.

It is to be understood that the disclosure described above and disclosed in the drawings is to be regarded only as a non-limiting example and that it is defined by the scope of the patent claims.

The invention claimed is:

1. A holder for a recording unit, where the holder comprises a first end and an opposite second end positioned along a longitudinal axis of the holder, where the recording unit is arranged with an interface having a defined shape configured to cooperate with an interface of a medicament delivery device and where the recording unit is configured for obtaining information regarding the use of the medicament delivery device, where the first end of the holder comprises an interface having a shape that corresponds to and cooperates with the defined shape of the interface of the recording unit, and where the second end of the holder comprises attachment elements for attaching the holder to a suitable surface.

2. The holder according to claim 1, further comprising a stand provided with said interface, onto which the recording unit may be removably attached.

3. The holder according to claim 1, wherein the interface of the holder comprises 3-D structures configured to positively engage with the interface of the recording unit.

4. The holder according to claim 1, further comprising a base, which base is arranged with said attachment elements.

5. The holder according to claim 4, wherein the base is arranged in a flexible material so as to adapt to the shape of the attaching surface.

6. The holder according to claim 1, wherein the attachment elements comprise a number of suction cups.

7. The holder according to claim 1, wherein the attachment elements comprise a micro-porous material.

8. The holder according to claim 1, wherein the attachment elements comprise adhesive tape.

9. The holder according to claim 1, wherein the attachment elements comprise hooks and loops.

10. The holder according to claim 1, wherein the attachment elements comprise a plurality of magnets.

11. The holder according to claim 1, further comprising an electronic circuit arranged operably connected to said recording unit when the recording unit is attached to the holder.

12. The holder according to claim 11, wherein said electronic circuit is arranged with user communication elements.

13. The holder according to claim 12, wherein said user communication elements comprise buttons where each button comprises a symbol indicative of the perceived health of the patient.

14. The holder according to claim 12, wherein said user communication elements comprise at least one display.

15. The holder according to claim 12, wherein the user communication elements comprise at least one display.

16. An assembly comprising:
a recording unit comprising an interface having a defined shape configured to cooperate with an interface of a medicament delivery device for obtaining information regarding the use of the medicament delivery device; and
a holder comprising a first end and an opposite second end positioned along a longitudinal axis of the holder,
an interface located on the first end of the holder comprising a shape that corresponds to and cooperates with the defined shape of the interface of the recording unit;
a stand configured as part of the interface of the holder to releasably attach the recording unit;
an electronic circuit operably associated with the holder interface and configured to electrically connect to the recording unit when the recording unit is attached to the holder; and
attachment elements located on the stand for attaching the second end of the holder to a suitable surface.

17. The assembly according to claim 16, wherein the stand comprises a base composed of a flexible material so as to adapt to the shape of the attaching surface.

18. The assembly according to claim 16, wherein said electronic circuit is arranged with user communication elements.

19. The assembly according to claim 16, wherein the holder further comprises user communication elements comprising a plurality of buttons, where each button comprises a symbol indicative of perceived health of a user of the recording unit.

\* \* \* \* \*